United States Patent [19]

Dubrous

[11] Patent Number: 5,429,866
[45] Date of Patent: Jul. 4, 1995

[54] METALLURGICAL SILICON POWDER EXHIBITING LOW SURFACE OXIDATION

[75] Inventor: Francis Dubrous, Sallanches, France

[73] Assignee: Pechiney Electrometallurgie, France

[21] Appl. No.: 161,460

[22] Filed: Dec. 6, 1993

Related U.S. Application Data

[63] Continuation of Ser. No. 819,176, Jan. 10, 1992, abandoned.

[30] Foreign Application Priority Data

Jan. 11, 1991 [FR] France ................. 91 00532

[51] Int. Cl.$^6$ ............................................. B32B 5/16
[52] U.S. Cl. ................................. 428/323; 428/331; 428/348; 428/403; 428/404
[58] Field of Search .............. 428/331, 403, 404, 401, 428/220, 335; 423/348, 323

[56] References Cited

U.S. PATENT DOCUMENTS

| | | | |
|---|---|---|---|
| 3,767,458 | 10/1973 | Moore, Jr. | 428/404 |
| 4,430,150 | 2/1984 | Levine et al. | 432/247 |
| 4,565,913 | 1/1986 | Yatsurugi et al. | |
| 4,637,855 | 1/1987 | Witter et al. | 423/348 |
| 4,871,117 | 10/1989 | Baueregger et al. | 241/23 |
| 5,069,740 | 12/1991 | Levine et al. | 423/348 |

OTHER PUBLICATIONS

Hackh's, Chemical Dictionary, p. 529 1987.

*Primary Examiner*—N. Edwards
*Attorney, Agent, or Firm*—Pollock, Vande Sande & Priddy

[57] ABSTRACT

Silicon or silicon alloy exhibiting low surface oxidation as a result of a surface silica layer of less than 2 nm, and production processes by means of grinding under a minimally-reactive atmosphere in the presence of an oil or by atomization in a vacuum or in a minimally-reactive gas under reduced pressure.

5 Claims, No Drawings

METALLURGICAL SILICON POWDER EXHIBITING LOW SURFACE OXIDATION

This is a Continuation of application Ser. No. 07/819,176, filed Jan. 10, 1992, now abandoned.

FIELD OF THE INVENTION

The invention concerns a metallurgical silicon powder exhibiting a very low surface oxidation, as well as the means for preparing and preserving this product.

BACKGROUND OF THE INVENTION

Metallurgical silicon is generally obtained by reduction of silica using carbon in a submerged arc electric furnace. The silicon produced in the liquid state is then cast in ingots whose weight may range from 10 to 1,000 kg. After solidification and cooling, the ingots may be crushed, then ground into a powder.

The grinding mills work most often in the open air. However, for reasons of safety, they may be placed in a reduced-oxygen atmosphere, e.g., one containing 5–10% $O_2$. In fact, the mixture of air and powdered silicon in the mills may entail risks of explosion.

To avoid the grinding operation, the liquid silicon may be atomized, thus directly producing a powder composed of coarsely spherical particles. This technique also makes it possible to reduce the size of the finest granulometric fractions and to ensure very rapid solidification, so as to promote formation of special crystalline structures.

These various methods make it possible to obtain various types of silicon differentiated by their crystalline structure, which depends on the solidification and cooling rate used. Different types of silicon may also be produced by adjusting the proportions of impurities and/or alloyed elements added in small quantities.

While the preparation method and composition allow silicon grades suitable for the intended use to be obtained, it emerges that surface oxidation on the particles forming the powder of said Si is still observed. This oxidation exists as a silica film covering the entire surface of said particles, and its thickness normally ranges between 3 and 5 nm (30 and 50 Å) but is virtually never less than 3 nm (30 Å). It may happen that, on rare occasions, thicknesses of silica of less than 3 nm (30 Å) are measured, but the processes for obtaining the Si powders described above do not make it possible to obtain such powders exhibiting low oxidation regularly and in a reproducible fashion, nor to ensure their surface quality.

In its applications, metallurgical silicon is often used as a raw material in heterogenous reactions, e.g., in the presence of a gas like methyl chloride for production of dichlorosilane in order to produce silicones, or in the presence of a liquid such as molten aluminum in order to manufacture an Al—Si alloy.

SUMMARY OF THE INVENTION

Applicant thus presumed that, whatever its use, a silicon having a very low surface oxygen content was desirable. For example, in the case of silicone manufacture, the silica layer which covers the silicon grains could only constitute a chemical barrier which slows the reactions with methyl chloride. In the case of Al—Si alloy manufacture, this silica layer could only be reduced by the aluminum, thus producing aluminum oxide which would necessarily be included in the final alloy.

To verify this and the consequences of this silica layer on the properties of the silicon, Applicant thus undertook research to discover a powdered silicon on which very limited surface oxidation significantly lower than the values observed on products according to prior art could be ensured.

DETAILED DESCRIPTION

The invention is a powdered metallurgical silicon or metallurgical silicon-based alloy powder exhibiting low surface oxidation, characterized by the fact that the particles composing the power are covered with a surface silica layer having a maximum thickness of 2 nm (20 Å).

It is found, unexpectedly, that the very thin silica layer according to the invention is the determining parameter making it possible to improve substantially the performance of the silicon in its applications: mainly the production of dimethyl dichlorosilane by reaction of the gaseous methyl chloride on the silicon, the first stage of silicone synthesis; but also the manufacture of the Al/Si alloy by adding Si to molten Al. The previously-known parameters (in particular the crystalline structure and the proportion of other elements) unquestionably remain important, but it is less noteworthy than that resulting from the silica layer according to the invention, as indicated by the results in Example 2.

The best results were obtained using a measurable silica layer, typically ranging between approximately 1 and 2 nm (10 and 20 Å). A layer of oxide of less than 1 nm (10 Å) proved less effective.

It appears that the important factor is not the total oxygen content of the silicon (for example, measured in parts per million of oxygen out of the total amount of silicon), but the thickness of the surface $SiO_2$ layer, or the surface oxygen content, which determines the performance parameters of the silicon, in particular it reaction speed with the methyl chloride.

The silicon powders according to the invention may comprise grains of very different sizes ranging from 0 to 30 mm. They prove particularly advantageous in the case of fine powders composed of particles measuring less than 350 $\mu$m, the finest powders showing the greatest sensitivity to oxidation.

The thickness of the surface oxide layer is measured by using Auger electron spectroscopy. This method makes it possible to perform an analysis of a surface layer whose thickness is approximately several nm. The sample for which the thickness of the surface layer is to be measured is subjected to successive analyses using Auger spectroscopy during ionic deoxidizing, which gradually removes the oxide layer. Successive analyses give a profile of oxygen concentration by giving the erosion rate. The erosion rate is determined by measuring the depth of the final crater (Talystep) or after calibration by measuring a completely known concentration profile of an $O_{15}$ isotope obtained by implantation.

Particles of metallurgical silicon according to the invention may be obtained by starting with metallurgical silicon ingots which have been preliminarily cast, preferably in an air-sealed arrangement, and crushed to 30 mm. The pieces obtained are then ground at ambient temperature under a minimally-reactive atmosphere, while adding, during the grinding operation, an oil which allows the new surfaces created by grinding to be covered and protected as soon as they emerge.

A mixture of nitrogen and air containing not more than 8% oxygen, which suffices to remove the risks of explosion in the mills, is also sufficient to obtain an Si powder according to the invention, after, of course, adding oil during the grinding operation. Pure, or technically pure nitrogen may also be suitable, but does not eliminate the need to add oil during grinding. The oil may be an alkane-type hydrocarbon, an ester, a glyceride, or, best of all, a silicon oil. The quantity added normally ranges between 0.1 and 0.5%, and preferably between 0.1 and 0.3%.

Silicon powders according to the invention may also be obtained by beginning with liquid metallurgical silicon by atomization in a vacuum or a minimally-reactive gas under reduced pressure, e.g., nitrogen or argon under reduced pressure, i.e., less than atmospheric pressure. In the case of nitrogen, the quantity of nitride formed on the surface of the particles is extremely small, and the little nitride formed has the advantage of not creating an even, continuous film, as does silica.

The particles obtained are then stored and preserved at ambient temperature, preferably under a protective atmosphere (nitrogen, argon, vacuum). In fact, re-exposure to air leads to a slow surface re-oxidation slowed by the film of oil, and thus to their transformation into a product off specifications.

The metallurgical silicon is produced according to conventional methods: carbothermia in the submerged arc furnace, then refining in a ladle, accompanied by determination of grade. Its typical composition is as follows:
Fe≦0.40%
Ca≦0.20%
Al≦0.20%
Si≧98%.

However, the invention is also applicable to Si-based alloys, in particular those used in the manufacture of silicones and containing, for example, one of the elements Fe, Al, Ca, or Cu, and in particular Cu, in a proportion of between 1 and 8%.

EXAMPLES

Examples 1

This example illustrates the production of the silicon powder according to the invention.

Using a 2t ladle of liquid Si, four ingots weighing approximately 500 kg each were cast in ingot molds equipped with movable covers to avoid contact between the liquid metal and the air.

The ingots were coarsely crushed, then placed in a beater mill swept by a gas current composed of a nitrogen-air mixture containing 8% oxygen. 0.3% liquid silicone oil (by weight) was added.

The ground product thus obtained was run through a sieve measuring 250 μm and is stored in a bag under an argon atmosphere.

The thickness of the silica layer was measured at 1.2 nm (12 Å) using Auger electron microscopy.

As a comparison, a new load was ground without adding oil to the mill, but retaining the other operating conditions.

A thickness of the silica layer of 3.5 nm (35 Å) was measured on the powdered silicon.

Example 2

In this example, the behavior of different Si powders was compared in reactions with methyl chloride giving dimethyldichlorosilane mixed with the other reaction products. For this purpose, in each test the silicon to be tested was placed at the bottom of a reaction vessel having an interior diameter of 35 mm, on a piece of sintered glass through which a current of gaseous methyl chloride obtained by volatilization of liquid methyl chloride at a flow rate of 7.83 g/h was passed. The reaction was effected at 300° C. under a pressure of 2 atmospheres, and air was drawn out of the reaction vessel before each operation by sweeping with argon. Tests were conducted using 50 g of powdered silicon measuring between 50 and 160 μm, mixed, on each occasion, with 3 g of atomized powdered copper having the same granulometry.

During each test, the reaction rate (v), as defined by the ratio of the weight of Si which reacted during a given interval to the original weight of Si, as well as the proportion (x) of dimethylchlorosilane mixed with the other reaction products, were recorded.

The conditions for production of powdered silicon and the results are given in the following table:

TABLE 1

| Test Number | Production of powdered Si | Thickness of the SiO$_2$ layer (nm) | Main impurities Ca % | Al % | Fe % | Rate (v) % | Proportion of dimethyl chlorosilane (x) % |
|---|---|---|---|---|---|---|---|
| Prior Art | | | | | | | |
| 1 | Si ground in open air (beater mill) | 4.5 | 0.08 | 0.21 | 0.37 | 70 | 85 |
| 2 | Si poured in granulated form in water, then ground in the open air | 5.5. | 0.12 | 0.19 | 0.34 | 72 | 83 |
| Invention | | | | | | | |
| 3 | Si ground under Ar atmosphere (beater mill) with 03% silicone oil | 1.2 | 0.8 | 0.21 | 0.39 | 88 | 86 |
| 4 | Si atomized in nitrogen under reduced pressure | 1.0 | 0.8 | 0.21 | 0.39 | 90 | 81 |

TABLE 1-continued

| Test Number | Production of powdered Si | Thickness of the SiO$_2$ layer (nm) | Main impurities Ca % | Al % | Fe % | Rate (v) % | Proportion of dimethyl chlorosilane (x) % |
| --- | --- | --- | --- | --- | --- | --- | --- |
| 5 | (350 mm of Hg) Si atomized in argon under reduced pressure (350 mm of Hg) | 0.5 | 0.8 | 0.21 | 0.39 | 77 | 80 |

It can be seen that, with a thin silica layer according to the invention, the reaction rate increases appreciably (25% gain) without reducing the rate of production of dimethyldichlorosilane. It can also be observed (Test 2) that a very energetic hardening of the silicon does not significantly improve the properties of the silicone, in comparison with the effect given by a thin oxide layer.

What is claimed is:

1. Metallurgical silicon or silicon-based alloy powder in the form of particles having a surface oxide layer exhibiting low surface oxidation, said surface oxide layer having a thickness no greater than 2 nm (20 Å).

2. Metallurgical silicon or silicon-based alloy powder in the form of particles having a surface oxide layer no thicker than 2 nm.

3. Powder according to claim 1, wherein said surface oxide layer has a thickness ranging between 1 and 2 nm (10 and 20 Å).

4. Powder according to claim 1 or 2, wherein said powder is an Si-based alloy containing copper.

5. Powder according to claim 1 or 2, wherein said powder is composed of particles measuring less than 350 μm.

* * * * *